US008692682B2

(12) United States Patent
Kimura et al.

(10) Patent No.: US 8,692,682 B2
(45) Date of Patent: Apr. 8, 2014

(54) POSITION DETECTION SYSTEM FOR DETECTION OBJECT AND POSITION DETECTION METHOD FOR DETECTION OBJECT

(75) Inventors: Atsushi Kimura, Tokyo (JP); Akio Uchiyama, Kanagawa (JP); Ryoji Sato, Tokyo (JP); Atsushi Chiba, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1177 days.

(21) Appl. No.: 12/441,631

(22) PCT Filed: Sep. 28, 2007

(86) PCT No.: PCT/JP2007/068937
§ 371 (c)(1),
(2), (4) Date: Aug. 19, 2009

(87) PCT Pub. No.: WO2008/038753
PCT Pub. Date: Apr. 3, 2008

(65) Prior Publication Data
US 2010/0060472 A1    Mar. 11, 2010

(30) Foreign Application Priority Data

Sep. 28, 2006   (JP) .................................. 2006-264614

(51) Int. Cl.
*G08B 21/00*           (2006.01)
(52) U.S. Cl.
USPC ........ 340/686.1; 324/200; 700/186; 338/32 R
(58) Field of Classification Search
USPC .......... 340/686.1, 687; 324/207.12, 200, 228; 700/186; 338/32 R
See application file for complete search history.

(56) References Cited

U.S. PATENT DOCUMENTS 5,727,552 A * 3/1998 Ryan .............................. 600/407
6,812,842 B2 * 11/2004 Dimmer ..................... 340/572.4
(Continued)

FOREIGN PATENT DOCUMENTS

| JP | 2005-245963 | 9/2005 |
| JP | 2006-026391 | 2/2006 |
| JP | 2006-192252 | 7/2006 |

OTHER PUBLICATIONS

Tokunaga, Y. et al., "Precision Position-Detecting System using LC Resonant Magnetic Marker", J. Magn. Soc. Jpn., vol. 29, No. 2, pp. 153-156 (2005).

(Continued)

*Primary Examiner* — George Bugg
*Assistant Examiner* — Edny Labbees
(74) *Attorney, Agent, or Firm* — Scully, Scott, Murphy & Presser, P.C.

(57) ABSTRACT

A position detection system for a detection object and a position detection method for a detection object that enable calibration without removing a detection object after the detection object is introduced into a detection space are provided. Provided are a magnetic-field generating unit (3) that generates a position-detection magnetic field; a detection object (5) including a resonant circuit (21) that generates a resonant magnetic field and an external-signal switch that connects or disconnects the path of the resonant circuit (21); a switch-controlling unit (7) that controls connecting or disconnecting of the external-signal switch; a position-detection-magnetic-field detecting unit (9) that detects the magnetic field strength of at least one of the position-detection magnetic field and the resonant magnetic field; and a position-calculating unit (11) that calculates the position and orientation of the detection object (5) based on a detection signal from the position-detection-magnetic-field detecting unit (9).

17 Claims, 9 Drawing Sheets

(56) References Cited

U.S. PATENT DOCUMENTS

| | | | |
|---|---|---|---|
| 7,751,866 B2 * | 7/2010 | Aoki et al. | 600/424 |
| 8,140,145 B2 * | 3/2012 | Kimura et al. | 600/424 |
| 8,554,335 B2 * | 10/2013 | Ameri et al. | 607/63 |
| 2003/0187347 A1 | 10/2003 | Nevo et al. | |
| 2003/0229268 A1 * | 12/2003 | Uchiyama et al. | 600/109 |
| 2005/0216231 A1 | 9/2005 | Aoki et al. | |
| 2005/0261570 A1 * | 11/2005 | Mate et al. | 600/411 |
| 2007/0185398 A1 | 8/2007 | Kimura et al. | |
| 2010/0322859 A1 * | 12/2010 | Jones et al. | 424/9.1 |

OTHER PUBLICATIONS

European Search Report dated Feb. 21, 2013 from corresponding European Patent Application No. 07 82 8679.6.

European Patent Convention Communication dated Oct. 9, 2013, from corresponding European Application No. EP 07 828 679.6.

* cited by examiner

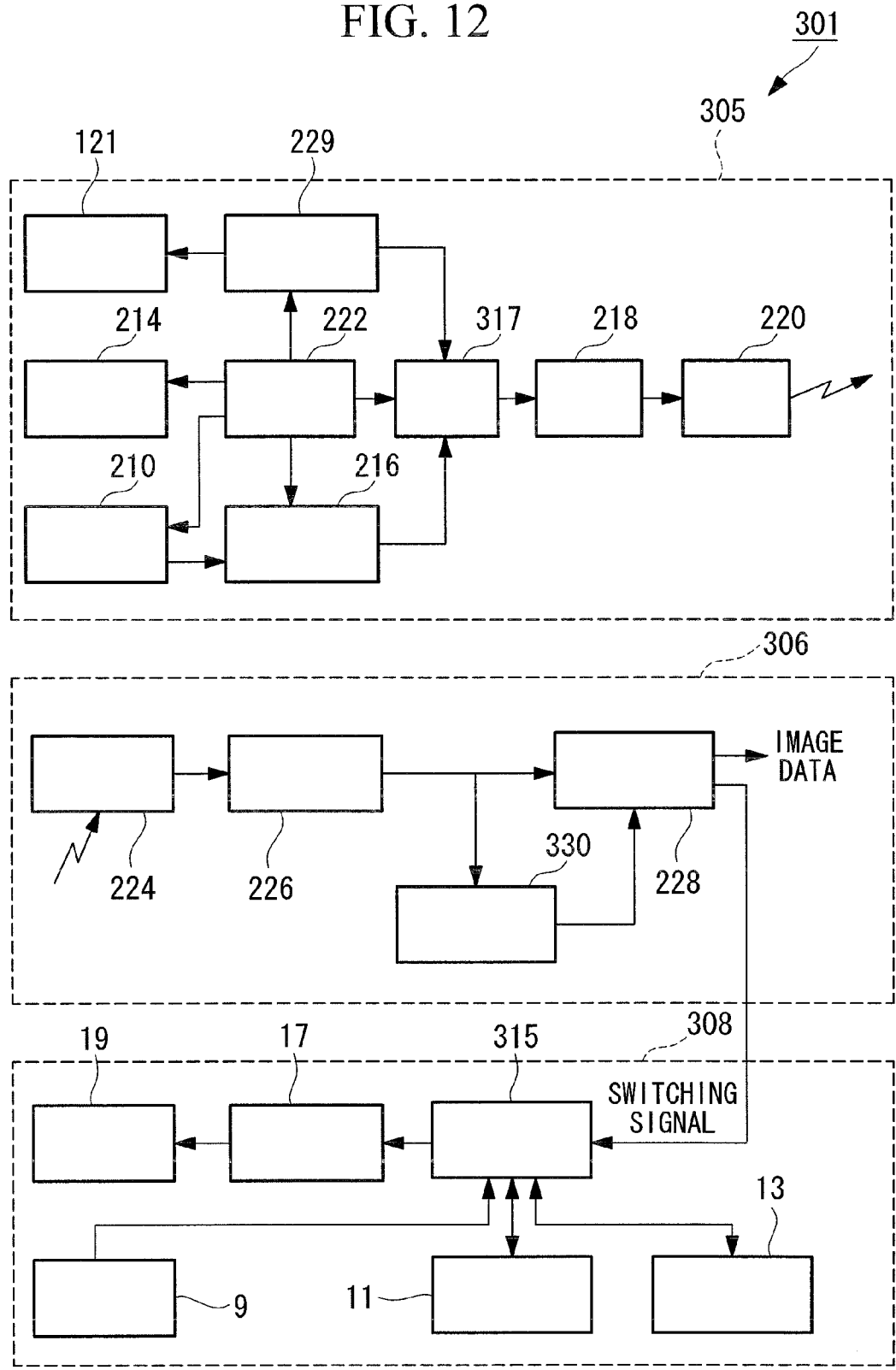

POSITION DETECTION SYSTEM FOR DETECTION OBJECT AND POSITION DETECTION METHOD FOR DETECTION OBJECT

TECHNICAL FIELD

The present invention relates to position detection systems for detection objects and position detection methods for detection objects.

BACKGROUND ART

A recently proposed position detection apparatus based on magnetic field detection creates a resonance state in an LC resonant circuit disposed in a detection object by supplying a magnetic field, acquires a magnetic field newly generated by the resonance through a plurality of magnetic field sensors, and detects the position and orientation of the detection object from the acquired information (see, for example, Patent Document 1 and Non-patent Document 1).

In the technique described in Patent Document 1 above, the magnetic field strength detected by the sensors includes both the magnetic field strength of a magnetic field generated toward the LC resonant circuit and accidentally reaching the sensors (ambient magnetic field) and the magnetic field strength of a magnetic field generated from the LC resonant circuit and reaching the sensors as intended (resonant magnetic field).

To remove the magnetic field strength of the ambient magnetic field accidentally reaching the sensors, before the position of the detection object is measured, the magnetic field strength of the ambient magnetic field is measured with the LC resonant circuit removed from a detection space where the position of the detection object can be detected (calibration). Afterwards, the magnetic field strength of the ambient magnetic field and the resonant magnetic field is measured with the LC resonant circuit introduced into the detection space, and the difference between that magnetic field strength and the magnetic field strength of the ambient magnetic field measured in the above calibration is determined to remove the magnetic field strength of the ambient magnetic field and determine the magnetic field strength of the resonant magnetic field.

This allows only the resonant magnetic field created by the LC resonant circuit to be collected to accurately calculate the position of the detection object.

Patent Document 1:
Japanese Unexamined Patent Application, Publication No. 2006-26391

Non-patent Document 1:
Tokunaga, Hashi, Yabukami, Kohno, Toyoda, Ozawa, Okazaki, and Arai, "Precision Position-Detecting System using LC Resonant Magnetic Marker", J. Magn. Soc. Jpn., Vol. 29, No. 2, pp. 153-156 (2005)

DISCLOSURE OF INVENTION

The above position detection method, however, has a problem in that, after the calibration, recalibration cannot be performed with the detection object remaining in the detection space.

Specifically, an error may occur in the calculated position of the detection object due to a difference between the magnetic field strength of the ambient magnetic field measured in the initial calibration and that of the ambient magnetic field used for position detection of the detection object, and recalibration may need to be performed to eliminate the above error. In such a case, the above position detection method has a problem in that calibration for detecting only the strength of the ambient magnetic field cannot be performed with the detection object remaining in the detection space.

One possible case where recalibration is required as described above is the case where the ambient magnetic field shows unexpected variations after the detection object is introduced into the detection space. Specific examples include temporal variations in the ambient magnetic field due to temperature drift of the position detection apparatus and variations in the ambient magnetic field due to mechanical displacement of the position detection apparatus itself.

Even if recalibration is possible after the detection object is recovered from the detection space, positional information calculated by the position detection apparatus is often used in introduction or recovery of the detection object. This can cause a problem in the recovery of the detection object because the detection object is recovered based on the positional information including the error preceding the recalibration.

An object of the present invention, which has been made to solve the above problems, is to provide a position detection system for a detection object and a position detection method for a detection object that enable calibration without removing a detection object after the detection object is introduced into the detection space.

To achieve the above object, the present invention provides the following solutions.

A first aspect of the present invention provides a position detection system for a detection object, including a magnetic-field generating unit including a position-detection-signal generating section that generates an alternating signal of predetermined frequency and a position-detection-magnetic-field generating section that generates a position-detection magnetic field based on the alternating signal; a detection object which includes a coil and a capacitor constituting a resonant circuit and an external-signal switch that connects or disconnects the path of the resonant circuit based on an external signal and which generates a resonant magnetic field by causing resonance when a current flows through the resonant circuit in response to the position-detection magnetic field; a switch-controlling unit including a switching-signal generating section that generates a switching signal for controlling connecting or disconnecting of the external-signal switch and a switching-signal transmitting section that transmits the generated switching signal to the external-signal switch by converting the switching signal into physical energy; a position-detection-magnetic-field detecting unit that detects the magnetic field strength of the position-detection magnetic field and the resonant magnetic field; a position-calculating unit that calculates the position and orientation of the detection object based on a detection signal from the position-detection-magnetic-field detecting unit; a memory that stores the detection signal from the position-detection-magnetic-field detecting unit; and a position-detection controlling unit that stores the detection signal from the position-detection-magnetic-field detecting unit in the memory separately divided into a detection signal resulting from detection of the position-detection magnetic field alone and a detection signal resulting from detection of the position-detection magnetic field and the resonant magnetic field.

According to the first aspect of the present invention, the connecting or disconnecting of the external-signal switch of the resonant circuit is controlled to control the generation of the resonant magnetic field while the position-detection magnetic field is being applied to the resonant circuit. That is, the resonant current induced in the resonant circuit is controlled to control the generation of the resonant magnetic field from the resonant circuit.

The external-signal switch connects or disconnects the path of the resonant circuit in response to the physical energy transmitted from the switch-controlling unit outside the detection object. The generation of the resonant magnetic field from the resonant circuit is thus externally controlled. The magnetic field strength of the resonant frequency alone is then calculated based on the difference between the magnetic field strength acquired by the position-detection-magnetic-field detecting unit before a switching operation for connecting or disconnecting the resonant circuit and the magnetic field strength acquired after the switching operation.

For example, a detection signal associated with the magnetic field strength, acquired before the switching operation, of the position-detection magnetic field alone is stored in the memory and the detection signal associated with the magnetic field strength acquired before the switching operation is read from the memory when determining the difference between the magnetic field strength of the position-detection magnetic field and the resonant magnetic field acquired after the switching operation, thus calculating the magnetic field strength of the resonant magnetic field alone. When the magnetic field strength acquired before the switching operation does not contain the magnetic field strength of the resonant magnetic field, the magnetic field strength acquired before the switching operation is stored in a calibration region of the memory. On the other hand, when the magnetic field strength acquired before the switching operation contains the magnetic field strength of the resonant magnetic field, the magnetic field strength acquired before the switching operation is stored in a measurement region of the memory.

Previous calibration data (magnetic field strength stored in the calibration region) does not necessarily have to be deleted but may be left in the memory as a record.

The position-detection controlling unit determines whether or not the magnetic field strength acquired by the position-detection-magnetic-field detecting unit contains the magnetic field strength of the resonant magnetic field, based on the switching signal output from the switching-signal generating section. The position-detection controlling unit writes the latest detection signal over the previous detection signal in the calibration region so that the detection signal, associated with the magnetic field strength, stored in the calibration region is always the latest data.

In the above invention, the external-signal switch preferably connects or disconnects the path of the resonant circuit in response to a switching signal converted into a magnetic field.

According to the present invention, the external-signal switch connects or disconnects the path of the resonant circuit in response to the magnetic field transmitted from the switch-controlling unit outside the detection object. This method reliably controls the external-signal switch as compared with a method in which the connecting or disconnecting of the external-signal switch is controlled in response to physical energy other than magnetic field, such as light or sound.

A second aspect of the present invention provides a position detection system for a detection object, including a magnetic-field generating unit including a position-detection-signal generating section that generates an alternating signal of predetermined frequency and a position-detection-magnetic-field generating section that generates a position-detection magnetic field based on the alternating signal; a detection object which includes a coil and a capacitor constituting a resonant circuit and an internal-signal switch that connects or disconnects the path of the resonant circuit based on an internal signal and which generates a resonant magnetic field by causing resonance when a current flows through the resonant circuit in response to the position-detection magnetic field; a switch-controlling unit disposed inside the detection object and including a switching-signal generating section that generates a switching signal for controlling connecting or disconnecting of the internal-signal switch; a position-detection-magnetic-field detecting unit that detects the magnetic field strength of the position-detection magnetic field and the resonant magnetic field; a position-calculating unit that calculates the position and orientation of the detection object based on a detection signal from the position-detection-magnetic-field detecting unit; a switching-signal extracting unit that extracts the switching signal by detecting a level change of the detection signal; a position-calculating unit that calculates the position and orientation of the detection object based on a detection signal from the position-detection-magnetic-field detecting unit; a memory that stores the detection signal from the position-detection-magnetic-field detecting unit; and a position-detection controlling unit that stores the detection signal from the position-detection-magnetic-field detecting unit in the memory separately divided into a detection signal resulting from detection of the position-detection magnetic field alone and a detection signal resulting from detection of the position-detection magnetic field and the resonant magnetic field.

According to the second aspect of the present invention, the connecting or disconnecting of the internal-signal switch of the resonant circuit is controlled to control the generation of the resonant magnetic field while the position-detection magnetic field is being applied to the resonant circuit. That is, the resonant current induced in the resonant circuit is controlled to control the generation of the resonant magnetic field from the resonant circuit.

The internal-signal switch connects or disconnects the path of the resonant circuit based on the switching signal output from the switch-controlling unit inside the detection object. The generation of the resonant magnetic field from the resonant circuit is thus autonomously controlled inside the detection object. The magnetic field strength of the resonant frequency alone is then calculated based on the difference between the magnetic field strength acquired by the position-detection-magnetic-field detecting unit before a switching operation for connecting or disconnecting the resonant circuit and the magnetic field strength acquired after the switching operation.

The position-detection controlling unit determines whether or not the magnetic field strength acquired by the position-detection-magnetic-field detecting unit contains the magnetic field strength of the resonant magnetic field, based on the switching signal extracted by the switching-signal extracting unit. That is, the switching-signal extracting unit is used to detect that the resonant circuit is disconnected because the output level of the position-detection-magnetic-field detecting unit changes as the resonant circuit is disconnected.

Thus, the position detection system for the detection object can be realized even if the system is configured so that the responsibility for switching lies inside the detection object and so that synchronization is established outside the detection object.

In the first or second aspect of the present invention, the position-detection controlling unit preferably controls the position-detection-signal generating section.

This allows the position-detection controlling unit to control the magnetic field strength, frequency, etc. of the position-detection magnetic field generated from the positiondetection-magnetic-field generating section. The resonant circuit of the detection object can therefore reliably generate a resonant magnetic field that can be detected by the position-detection-magnetic-field detecting unit, as compared with the case where the position-detection controlling unit does not control the magnetic field strength etc. of the position-detection magnetic field.

The position detection system and method of the present invention for the detection object provide the advantage of enabling calibration without removing the detection object after the detection object is introduced into a detection space because the connecting or disconnecting of the external-signal switch of the resonant circuit is controlled to control the generation of the resonant magnetic field while the position-detection magnetic field is being applied to the resonant circuit.

BRIEF DESCRIPTION OF DRAWINGS

FIG. 12 is a block diagram outlining a modification of the position detection system in FIG. 11.

Figure 1:
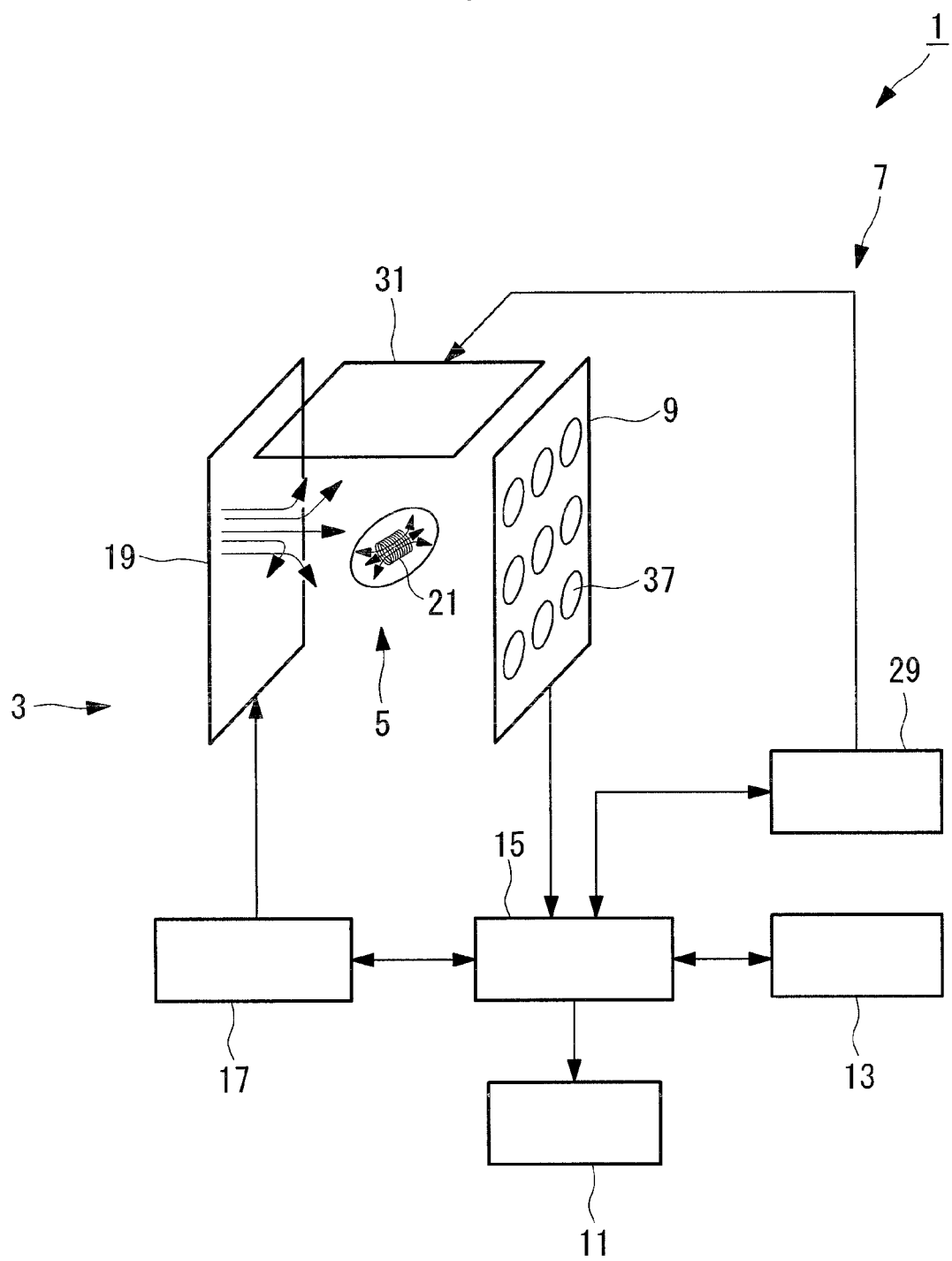
FIG. 1 is a schematic diagram outlining a position detection apparatus according to a first embodiment of the present invention.

EXPLANATION OF REFERENCE SIGNS 1, 101, 201, 301: position detection system (position detection system for detection object)
3: magnetic-field generating unit (detection-magnetic-field generating unit)
5, 105, 205, 305: detection object
7: switch-controlling unit
9: position-detection-magnetic-field detecting section
11: position-calculating unit
13: memory
15, 115, 215: position-detection controlling unit
17: position-detection-signal generating section
19: position-detection-magnetic-field generating section
21, 121: resonant circuit
23: coil
27: external-signal switch
29, 229: switching-signal generating section 31: switching-signal transmitting section
112: switching-signal extracting unit
127: internal-signal switch
129: switching-signal generating section (switch-controlling unit)

BEST MODE FOR CARRYING OUT THE INVENTION

First Embodiment

A first embodiment according to a position detection system of the present invention will now be described with reference to FIGS. 1 to 4.

FIG. 1 is a schematic diagram outlining a position detection apparatus according to this embodiment.

As shown in FIG. 1, a position detection system (position detection system for a detection object) 1 includes a magnetic-field generating unit (detection-magnetic-field generating unit) 3 that generates an alternating magnetic field for detecting the position of a detection object 5; the detection object 5, which generates a resonant magnetic field in response to the position-detection magnetic field; a switch-controlling unit 7 that controls the generation of the resonant magnetic field from the detection object 5; a position-detection-magnetic-field detecting unit 9 that detects the magnetic field strength of the position-detection magnetic field, or the magnetic field strength of the position-detection magnetic field and the resonant magnetic field; a position-calculating unit 11 that calculates the position and orientation of the detection object 5 based on a detection signal from the position-detection-magnetic-field detecting unit 9; a memory 13 that stores the detection signal; and a position-detection controlling unit 15 that controls, for example, a position-detection-signal generating section 17, as described below, the position-calculating unit 11, and the memory 13.

The magnetic-field generating unit 3 includes the position-detection-signal generating section 17, which generates an alternating signal, and a position-detection-magnetic-field generating section 19 that generates the position-detection magnetic field based on the alternating signal.

The alternating signal generated by the position-detection-signal generating section 17 is, for example, an alternating current whose frequency, preferably, substantially agrees with the resonant frequency of a resonant circuit 21, as described later, in the detection object 5. The position-detection controlling unit 5 feeds a control signal to the position-detection-signal generating section 17 to control, for example, the frequency or amplitude of the alternating signal.

The position-detection-magnetic-field generating section 19 generates the position-detection magnetic field, which is an alternating magnetic field, based on the supplied alternating signal, and can be exemplified by one constituted of a coil. The position-detection-magnetic-field generating section 19 is disposed so as to form the position-detection magnetic field over an entire detection space S for the detection object 5. Although the configuration in which the single position-detection-magnetic-field generating section 19 is disposed is described as an example in this embodiment, a plurality of position-detection-magnetic-field generating sections 19 may be arranged around the detection space S; the configuration used is not particularly limited.

Figure 2:
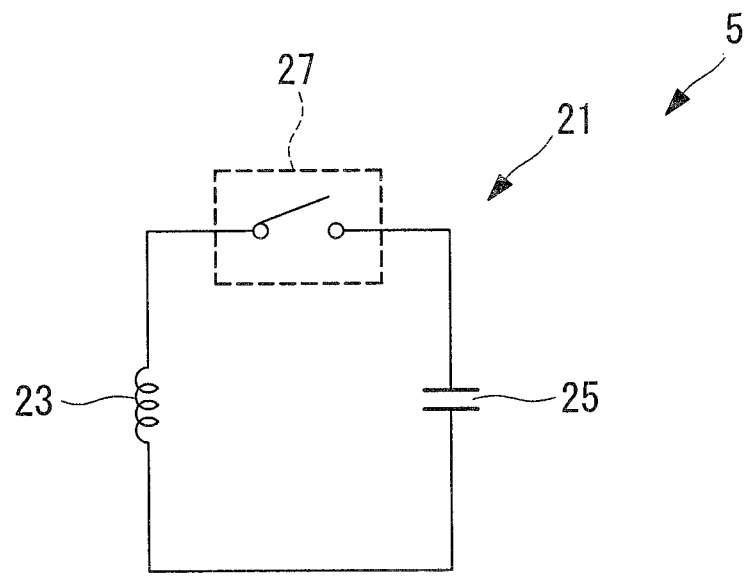
FIG. 2 is a diagram outlining the configuration of a detection object in FIG. 1.

FIG. 2 is a diagram outlining the configuration of the detection object 5 in FIG. 1.

The detection object 5 can be exemplified by a capsule medical device that is introduced into the body of, for example, a human subject for a medical procedure.

As shown in FIG. 2, the detection object 5 includes the resonant circuit 21, which generates the resonant magnetic field in response to the position-detection magnetic field, and the resonant circuit 21 includes a coil 23 and a capacitor 25 constituting a series resonant circuit and an external-signal switch 27 that connects and disconnects the path of the resonant circuit 21.

The resonant circuit 21 generates the resonant magnetic field in response to a position-detection magnetic field whose frequency substantially agrees with the resonant frequency determined by the coil 23 and the capacitor 25.

The external-signal switch 27 connects (ON) or disconnects (OFF) the resonant circuit 21 in response to a switching magnetic field formed by a switching-signal transmitting section 31, as described later, and is exemplified by a magnetic reed switch. The external-signal switch 27 is configured to be switched OFF if the magnetic field strength of the switching magnetic field exceeds a level specified for each switch.

The switch-controlling unit 7, as shown in FIG. 1, includes a switching-signal generating section 29 that generates a switching signal for ON/OFF control of the external-signal switch 27 (see FIG. 2) and the switching-signal transmitting section 31, which generates the switching magnetic field based on the switching signal.

The switching signal generated by the switching-signal generating section 29 is of two types, namely, High and Low. The external-signal switch 27 is switched OFF if the switching signal is High and is switched ON if the switching signal is Low. The switching signal is fed to the switching-signal transmitting section 31, as described above, and is also fed to the position-detection controlling unit 15 to, for example, calculate the position of the detection object 5.

Figure 3:
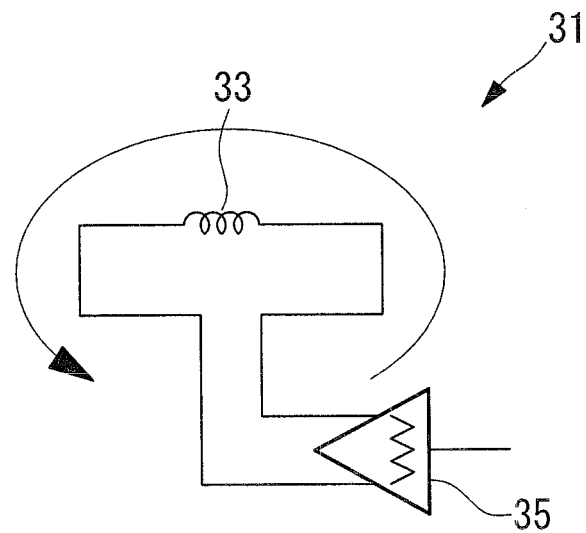
FIG. 3 is a diagram outlining the configuration of a switching-signal transmitting section in FIG. 1.

FIG. 3 is a diagram outlining the configuration of the switching-signal transmitting section 31 in FIG. 1.

As shown in FIG. 3, the switching-signal transmitting section 31, which generates the switching magnetic field based on the switching signal, includes a closed circuit constituted of a transmission coil 33 and an amplifier 35. The transmission coil 33 is supplied with a current from the amplifier 35 based on the switching signal. The switching-signal transmitting section 31 is disposed so as to form the switching magnetic field over the entire detection space S. Although the configuration in which the single switching-signal transmitting section 31 is disposed is described as an example in this embodiment, a plurality of switching-signal transmitting sections 31 may be arranged around the detection space S; the configuration used is not particularly limited.

The position-detection-magnetic-field detecting unit 9, as shown in FIG. 1, is constituted of a plurality of detection coils 37, each of which is electrically connected to the position-detection controlling unit 15. The detection coils 37 each output a corresponding detection signal in response to the magnetic field strength of the position-detection magnetic field alone (during calibration) or the magnetic field strength of the position-detection magnetic field and the resonant magnetic field (during position measurement).

The position-calculating unit 11 calculates the position and orientation of the detection object 5 based on a detection signal from the position-detection-magnetic-field detecting unit 9 during calibration and a detection signal from the position-detection-magnetic-field detecting unit 9 during position measurement.

The detection signal from the position-detection-magnetic-field detecting unit 9 during calibration and the detection signal from the position-detection-magnetic-field detecting unit 9 during position measurement are input to the position-calculating unit 11 via the position-detection controlling unit 15.

Formed in the memory 13 are a calibration region (not shown) that stores the detection signal from the position-detection-magnetic-field detecting unit 9 during calibration and a measurement region (not shown) that stores the detection signal from the position-detection-magnetic-field detecting unit 9 during position measurement.

The detection signal from the position-detection-magnetic-field detecting unit 9 during calibration and the detection signal from the position-detection-magnetic-field detecting unit 9 during position measurement are stored in the calibration region or the measurement region according to an instruction from the position-detection controlling unit 15.

The position-detection controlling unit 15 generates a control signal for controlling the frequency or amplitude of the alternating signal generated by the position-detection-signal generating section 17. It determines whether the detection signal from the position-detection-magnetic-field detecting unit 9 is a detection signal during calibration or during position measurement based on the switching signal generated by the switching-signal generating section 29.

Next, a calibration method and a position detection method for the position detection system 1 having the above configuration will be described.

First, as shown in FIG. 1, calibration is performed before the detection object 5 is introduced into the detection space S of the position detection system 1.

Specifically, an alternating signal is input from the position-detection-signal generating section 17 to the position-detection-magnetic-field generating section 19, which then generates a position-detection magnetic field. The position-detection-magnetic-field detecting unit 9 detects the generated position-detection magnetic field and outputs a detection signal corresponding to the magnetic field strength of the position-detection magnetic field. The detection signal is stored in the calibration region of the memory 13 via the position-detection controlling unit 15.

Subsequently, the detection object 5 is introduced into the detection space S, followed by position detection of the detection object 5.

During the position detection of the detection object 5, a Low switching signal is input from the switching-signal generating section 29 to the switching-signal transmitting section 31. If the switching signal is Low, the switching-signal transmitting section 31 generates no switching magnetic field.

At the same time, the switching signal is input to the position-detection controlling unit 15. This allows the position-detection controlling unit 15 to realize that the position detection of the detection object 5 is underway.

While the switching signal is Low, the circuit including the switching-signal transmitting section 31 is not disconnected.

The switching-signal transmitting section 31, as shown in FIG. 3, typically includes the transmission coil 33 and the amplifier 35 and forms a closed circuit with a low output impedance of the amplifier 35. Passage of each magnetic field for position detection through the transmission coil 33 generates a component that cancels out the magnetic field for position detection. For example, if the closed circuit were formed or not formed, depending on the switching signal, the environment around the position-detection magnetic field would vary.

The environment around the position-detection magnetic field, however, does not vary because the circuit constituted of the transmission coil 33 and the amplifier 35 is not disconnected.

The resonant circuit 21 of the detection object 5, as shown in FIG. 2, generates a resonant magnetic field in response to the position-detection magnetic field because the external-signal switch 27 is connected. That is, the resonant circuit 21 generates a resonant current in response to the alternating magnetic field, generated from the magnetic-field generating unit 3, whose frequency is substantially equal to the resonant frequency of the resonant circuit 21. This resonant current causes the coil 23 of the resonant circuit 21 to generate a resonant magnetic field.

The position-detection magnetic field generated from the magnetic-field generating unit 3 and the resonant magnetic field generated from the resonant circuit 21 are detected when passing through the detection coils 37 of the position-detection-magnetic-field detecting unit 9. The detection coils 37 output a detection signal corresponding to the magnetic field strength of the magnetic field passing therethrough to the position-detection controlling unit 15.

The position-detection controlling unit 15 outputs the detection signal detected during the position measurement to the position-calculating unit 11 and also outputs the detection signal detected during the calibration from the memory 13 to the position-calculating unit 11.

The position-calculating unit 11 extracts a detection signal associated with the magnetic field strength of the resonant magnetic field alone based on the two input detection signals. The extracted detection signal is used to calculate the position and orientation of the detection object 5.

A feature of this embodiment, namely, the method for calibration after the introduction of the detection object 5 into the operating region, will now be described.

If recalibration is required during the position detection of the detection object 5, as shown in FIG. 1, the switching-signal generating section 29 of the switch-controlling unit 7 outputs a High switching signal. The High switching signal is simultaneously output to the position-detection controlling unit 15 so that it realizes that recalibration is underway.

In the switching-signal transmitting section 31, to which the switching signal has been input, as shown in FIG. 3, the transmission coil 33 is supplied with a current from the amplifier 35 to generate a switching magnetic field.

In response to the switching magnetic field, the external-signal switch is disconnected, and the resonant circuit 21 is disconnected accordingly. Because no resonant current flows through the disconnected resonant circuit 21, it generates no resonant magnetic field even if a position-detection magnetic field is applied thereto.

Figure 4:
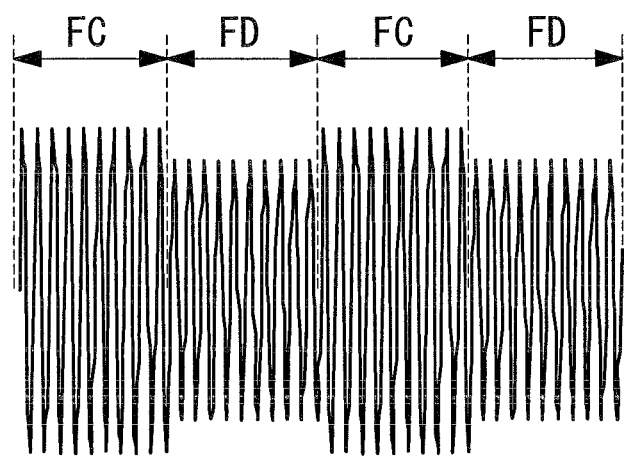
FIG. 4 is a schematic diagram showing variations in a detection signal from a position-detection-magnetic-field detecting unit in FIG. 1.

FIG. 4 is a schematic diagram showing variations in the detection signal from the position-detection-magnetic-field detecting unit 9 in FIG. 1. In FIG. 4, the vertical axis indicates voltage change, whereas the horizontal axis indicates passage of time.

Because only the position-detection magnetic field generated from the magnetic-field generating unit 3 passes through the detection coils 37 of the position-detection-magnetic-field detecting unit 9, they output a detection signal associated with the magnetic field strength of the position-detection magnetic field. FIG. 4 shows a detection signal during calibration (FC) and a detection signal during position detection (FD). This shows that the voltage amplitude corresponding to the detection signal during position detection (FD) is lower because the position-detection magnetic field and the resonant magnetic field interfere, whereas the voltage amplitude corresponding to the detection signal during calibration (FC) is higher because the above interference does not occur.

The detection signal from the detection coils 37 is stored in the calibration region of the memory 13 via the position-detection controlling unit 15. The detection signal acquired this time is then written over the detection signal acquired in the previous calibration. The detection signal stored by overwriting is used for subsequent calculation of the position and orientation of the detection object 5.

Afterwards, a Low switching signal is input again from the switching-signal generating section 29 to the switching-signal transmitting section 31, followed by position detection of the detection object 5.

With the above configuration, the connecting or disconnecting of the external-signal switch 27 of the resonant circuit 21 is controlled to control the generation of the resonant magnetic field while the position-detection magnetic field is being applied to the resonant circuit 21. That is, the resonant current induced in the resonant circuit 21 is controlled to control the generation of the resonant magnetic field from the resonant circuit 21. This enables calibration without removing the detection object 5 after the detection object 5 is introduced into the detection space S.

The external-signal switch 27 connects or disconnects the path of the resonant circuit 21 in response to the switching magnetic field generated from the switch-controlling unit 7 outside the detection object 5. The generation of the resonant magnetic field from the resonant circuit 21 can thus be controlled from outside the detection object 5. Hence, the magnetic field strength of the resonant frequency alone can be calculated based on the difference between the magnetic field strength acquired by the position-detection-magnetic-field detecting unit 9 before a switching operation for connecting or disconnecting the resonant circuit 21 and the magnetic field strength acquired after the switching operation, so that the position and orientation of the detection object 5 can be calculated.

The position-detection controlling unit 15 can determine whether or not the magnetic field strength acquired by the position-detection-magnetic-field detecting unit 9 contains the magnetic field strength of the resonant magnetic field, based on the switching signal output from the switching-signal generating section 29. Hence, the magnetic field strength of the resonant frequency alone can be calculated, so that the position and orientation of the detection object 5 can be calculated.

It can readily be determined when and to which state the external-signal switch 27 is switched because its switching timing is generated by the switching-signal generating section 29. Accordingly, if the switching signal is High (the switching magnetic field is applied), the detection signal is determined to be a calibration voltage. If the switching signal is Low, the detection signal is determined to be a measurement voltage, and only the magnetic field generated from the resonant circuit 21 can be acquired by determining the difference between the two signals. This enables calibration after the introduction of the detection object 5.

Because the position-detection controlling unit 15 controls the magnetic field strength, frequency, etc. of the position-detection magnetic field generated from the position-detection-magnetic-field generating section 19, the resonant circuit 21 of the detection object 5 can reliably generate a resonant magnetic field that can be detected by the position-detection-magnetic-field detecting unit 9, as compared with the case where the position-detection controlling unit 15 does not control the magnetic field strength etc. of the position-detection magnetic field.

Although the external-signal switch 27 used in the embodiment described above is a switch that responds directly to the energy of the switching magnetic field, it may instead be a switch that responds to another type of energy. The external-signal switch 27 used may be, for example, a switch that responds to the energy of light or sound; the type of switch is not particularly limited.

In practice, the measurement of the ambient magnetic field may be considered imperfect because copper forming a coil or a magnetic member constituting the detection object 5 can be present in the detection space S. The S/N, however, can be satisfactorily maintained within a practical range because the magnetic field to be acquired, which is radiated by resonance, has a high magnetic field strength. This permits calibration without removing the detection object 5 from the detection space S.

Although the present invention is applied to a position detection system that only detects the position and orientation of a detection object in the embodiment described above, it can also be applied to a position detection/guidance system that controls the posture of a detection object by means of a magnetic field.

As described in Patent Document 1, for example, the posture of the detection object may be controlled by mounting, for example, a permanent magnet in the detection object and applying an external magnetic field.

For such a configuration, the switching magnetic field used for ON/OFF control of the resonant circuit preferably has a higher frequency than the magnetic field for controlling the posture of the detection object. The use of such a magnetic field prevents the resonant circuit from being accidentally switched ON or OFF by the magnetic field for posture control. The switching magnetic field does not disturb the posture of the detection object because the detection object cannot follow changes in a magnetic field of high frequency, such as those in the switching magnetic field.

Specifically, a circuit that detects a switching signal of high frequency may be added to operate the external-signal switch by the output of the circuit. It is also possible to specify the generation pattern of the switching magnetic field and to add a circuit that does not respond to other magnetic fields.

Second Embodiment

Next, a second embodiment of the present invention will be described with reference to FIGS. 5 to 10.

A position detection system of this embodiment has the same basic configuration as that of the first embodiment, but differs from that of the first embodiment in the method for controlling the resonant magnetic field. In this embodiment, therefore, only the method for controlling the resonant magnetic field will be described using FIGS. 5 to 10, and the other components etc. will not be described.

Figure 5:
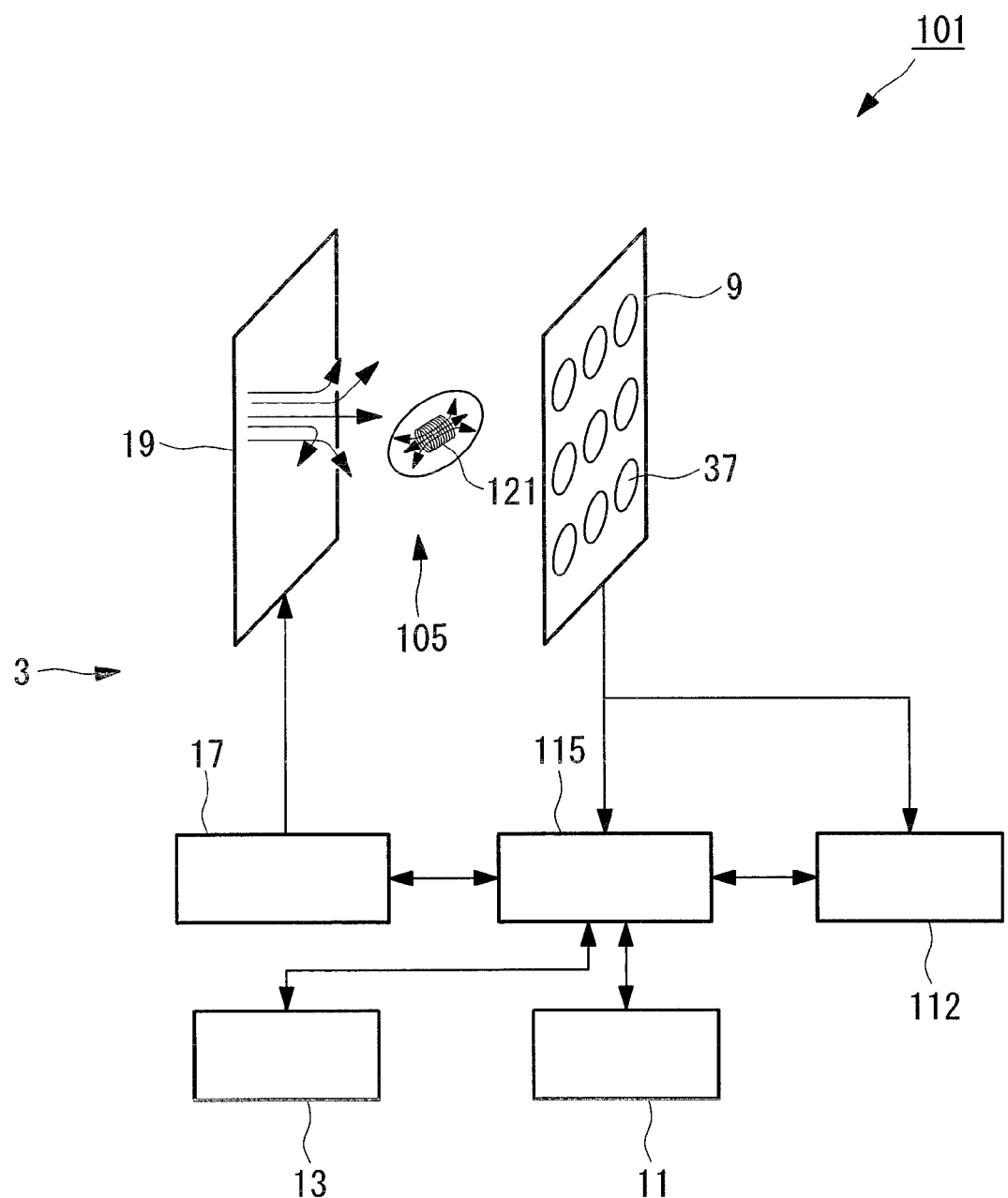
FIG. 5 is a schematic diagram outlining a position detection apparatus according to a second embodiment of the present invention.

FIG. 5 is a schematic diagram outlining a position detection apparatus according to this embodiment.

As shown in FIG. 5, a position detection system (position detection system for a detection object) 101 includes a magnetic-field generating unit 3 that generates an alternating magnetic field for detecting the position of a detection object 105; the detection object 105, which generates a resonant magnetic field in response to the position-detection magnetic field; a position-detection-magnetic-field detecting unit 9 that detects the magnetic field strength of the position-detection magnetic field, or the magnetic field strength of the position-detection magnetic field and the resonant magnetic field; a position-calculating unit 11 that calculates the position and orientation of the detection object 105 based on a detection signal from the position-detection-magnetic-field detecting unit 9; a switching-signal extracting unit 112 that extracts a switching signal from the detection signal by detecting a level change of the detection signal; a memory 13 that stores the detection signal; and a position-detection controlling unit 115 that controls, for example, the position-calculating unit 11 and the memory 13.

Figure 6:
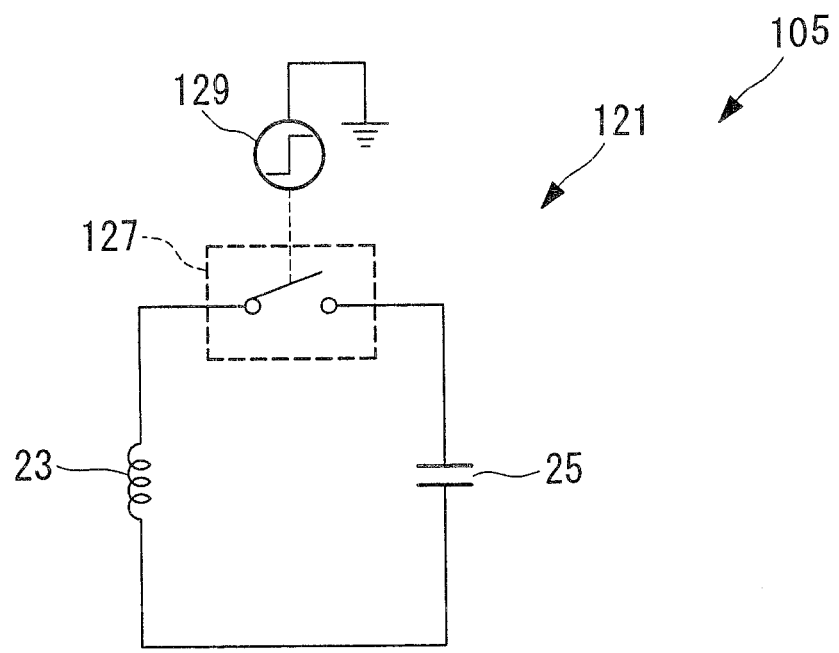
FIG. 6 is a diagram outlining the configuration of a detection object in FIG. 5.

FIG. 6 is a diagram outlining the configuration of the detection object 105 in FIG. 5.

The detection object 105 can be exemplified by a capsule medical device that is introduced into the body of, for example, a human subject for a medical procedure.

As shown in FIG. 6, the detection object 105 includes a resonant circuit 121 which generates the resonant magnetic field in response to the position-detection magnetic field and which includes a coil 23 and a capacitor 25 constituting a series resonant circuit, an internal-signal switch 127 that connects and disconnects the path of the resonant circuit 121, and a switching-signal generating section (switch-controlling unit) 129 that switches the internal-signal switch 127.

The resonant circuit 121 generates the resonant magnetic field in response to a position-detection magnetic field whose frequency substantially agrees with the resonant frequency determined by the coil 23 and the capacitor 25.

The switching-signal generating section 129 alternately outputs High and Low switching signals at its own timing, and the internal-signal switch 127 is connected or disconnected based on the switching signal.

Figure 7:
FIG. 7 is a diagram illustrating a switching signal extracted by a switching-signal extracting unit in FIG. 5.

FIG. 7 is a diagram illustrating the switching signal extracted by the switching-signal extracting unit 112 in FIG. 5.

The switching-signal extracting unit 112, as shown in FIG. 7, extracts the switching signal output from the switching-signal generating section 129 based on amplitude changes (level changes) of the detection signal output from the position-detection-magnetic-field detecting unit 9. Specifically, the switching-signal extracting unit 112 extracts high-amplitude portions and low-amplitude portions from the detection signal from the position-detection-magnetic-field detecting unit 9, and the position-detection controlling unit 115 determines that calibration is underway in the high-amplitude portions and that position detection of the detection object 105 is underway in the low-amplitude portions.

Next, a feature of the position detection system 101 according to this embodiment, namely, the method for calibration after the introduction of the detection object 105 into the operating region, will be described. The calibration method and the position detection method according to this embodiment will not be described because they are similar to those of the first embodiment.

If the detection object 105 is activated, as shown in FIG. 6, the switching-signal generating section 129 alternately outputs High and Low switching signals at a predetermined timing. These switching signals are input to the internal-signal switch 127 to switch the resonant circuit 121 ON or OFF. If the resonant circuit 121 is switched OFF, it generates no resonant magnetic field even if the position-detection magnetic field is applied thereto.

Alternately repeated are the state in which only the position-detection magnetic field generated from the magnetic-field generating unit 3 passes through the detection coils 37 of the position-detection-magnetic-field detecting unit 9 and the state in which the position-detection magnetic field and the resonant magnetic field pass through the detection coils 37 of the position-detection-magnetic-field detecting unit 9. The detection coils 37 output two different detection signals alternately depending on the state of the magnetic field passing therethrough at that time (see FIG. 4).

The two detection signals are input to the switching-signal extracting unit 112 and the position-detection controlling unit 115.

The switching-signal extracting unit 112, as shown in FIG. 7, extracts the switching signal from changes in the amplitude of the input detection signals and outputs the extracted switching signal to the position-detection controlling unit 115.

Based on the switching signal, the position-detection controlling unit 115 determines whether the input detection signal is the one detected during calibration or the one detected during position detection. The detection signal detected during calibration is stored in the calibration region of the memory 13, whereas the detection signal detected during position detection is stored in the measurement region.

The detection signal acquired this time is then written over the detection signal acquired in the previous calibration. The detection signal stored by overwriting is used for subsequent calculation of the position and orientation of the detection object 105.

With the above configuration, the connecting or disconnecting of the internal-signal switch 127 of the resonant circuit 121 is controlled to control the generation of the resonant magnetic field while the position-detection magnetic field is being applied to the resonant circuit 121. That is, the resonant current induced in the resonant circuit 121 is controlled to control the generation of the resonant magnetic field from the resonant circuit 121. This enables calibration without removing the detection object 105 after the detection object 105 is introduced into the detection space S.

The internal-signal switch 127 connects or disconnects the path of the resonant circuit 121 based on the switching signal output from the switching-signal generating section 129 inside the detection object 105. The generation of the resonant magnetic field from the resonant circuit 121 can thus be autonomously controlled inside the detection object 105. The magnetic field strength of the resonant frequency alone can then be calculated based on the difference between the magnetic field strength acquired by the position-detection-magnetic-field detecting unit 9 before a switching operation for connecting or disconnecting the resonant circuit 121 and the magnetic field strength acquired after the switching operation, so that the position and orientation of the detection object 105 can be calculated.

The position-detection controlling unit 115 can determine whether or not the magnetic field strength acquired by the position-detection-magnetic-field detecting unit 9 contains the magnetic field strength of the resonant magnetic field, based on the switching signal extracted by the switching-signal extracting unit 112. That is, the switching-signal extracting unit 112 is used to detect that the resonant circuit 121 is disconnected because the amplitude of the detection signal from the position-detection-magnetic-field detecting unit 9 changes as the resonant circuit 121 is disconnected.

Thus, the position detection system for the detection object 105 can be realized even if the system is configured so that the responsibility for switching lies inside the detection object 105 and so that synchronization is established outside the detection object 105.

If the output (e.g., amplitude) of the detection signal of the resonant magnetic field detected by the position-detection-magnetic-field detecting unit 9 is high, the switching timing of the internal-signal switch 127 may be constantly detected; if such continuous control makes synchronization (following the switching timing) incomplete because of a very low output level (e.g., low amplitude), it is also possible to establish synchronization only once at the beginning or intermittently. For example, a method may be used in which synchronization is established when the detection object 105 is introduced into the detection space S.

Figure 8:
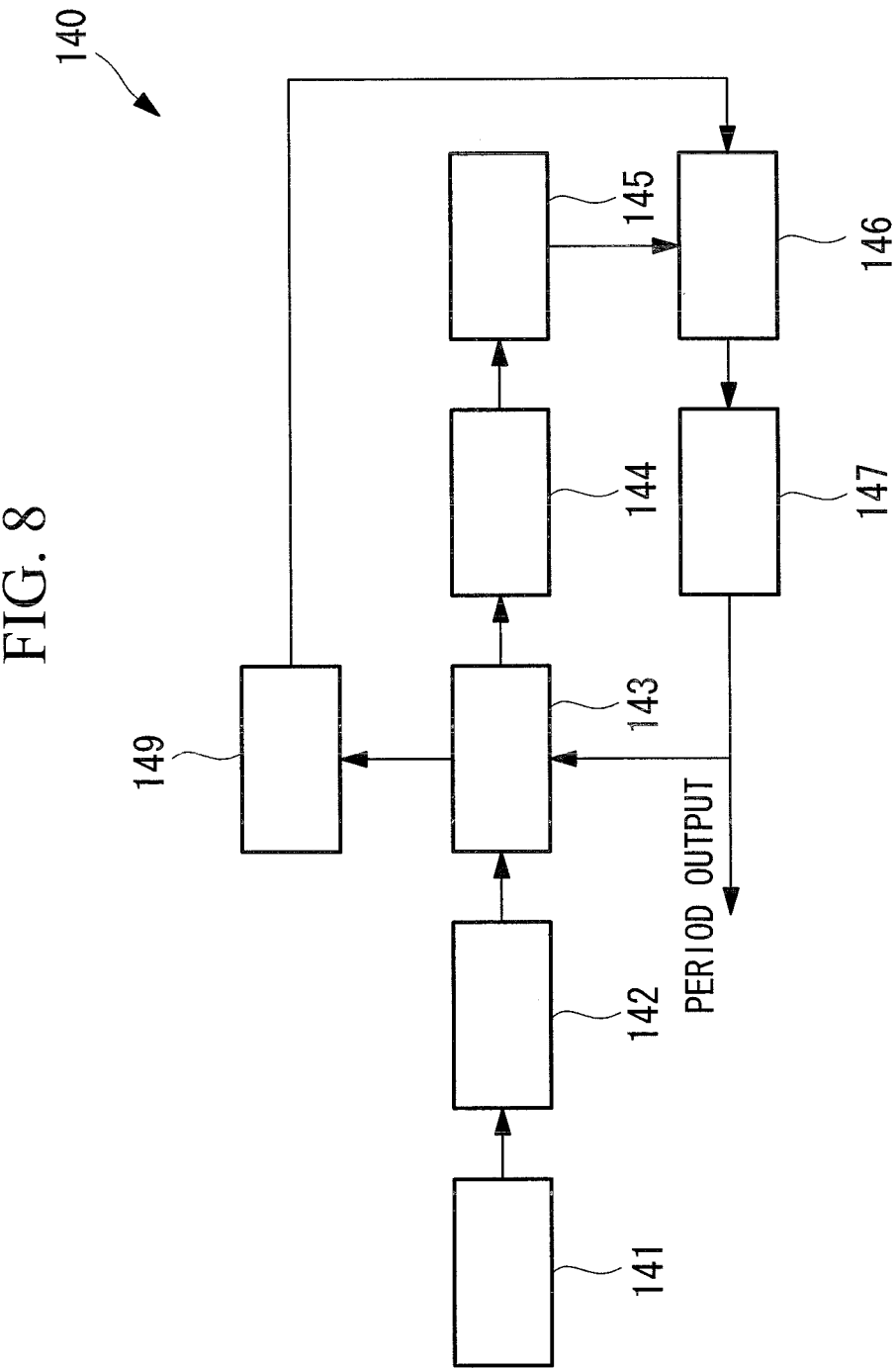
FIG. 8 is a diagram illustrating a configuration according to another example of a position-detection controlling unit in FIG. 5.

FIG. 8 is a diagram illustrating a configuration according to another example of the position-detection controlling unit in FIG. 5.

Alternatively, the position-detection controlling unit 115 may include a circuit that oscillates at the same time intervals as the switching-signal generating section 129 to form a phase-locked loop (PLL) 140 as shown in FIG. 8 once or at any point in time. The PLL 140 used may be a common one and is not particularly limited.

The PLL 140 includes a timing extractor 141, a frequency divider 142, a phase comparator 143, a charge pump 144, a low-pass filter (LPF) 145, a voltage holder 146, a voltage-controlled oscillator (VCO) 147, and a lock detector 149.

The PLL 140 can be applied to this embodiment by configuring it so that the output of the LPF 145 is temporarily maintained or switched to a voltage generator of equal voltage.

Figure 9:
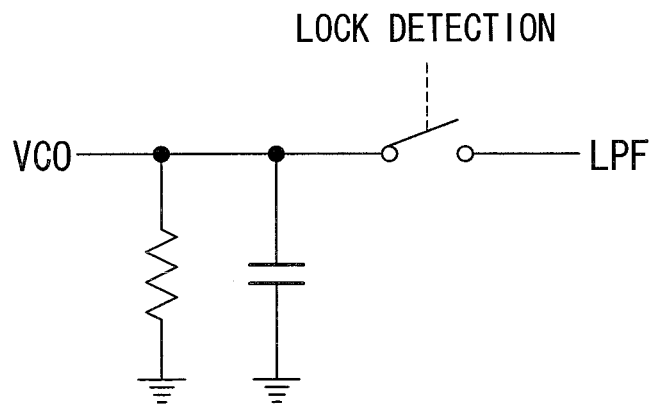
FIG. 9 is a diagram illustrating the configuration of a PLL portion in FIG. 8.
Figure 10:
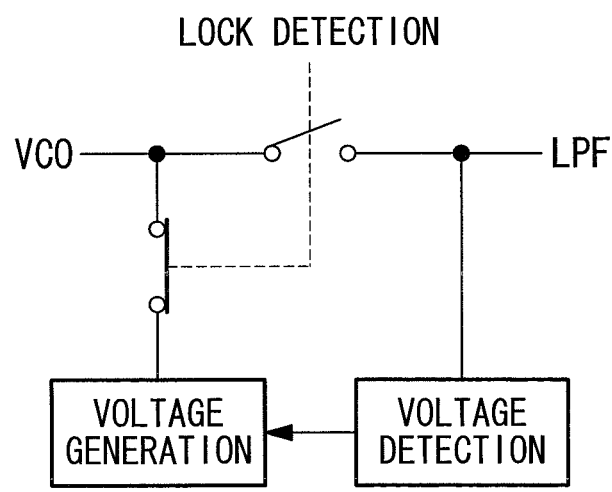
FIG. 10 is a diagram illustrating a configuration different from that of FIG. 9.

FIG. 9 is a diagram illustrating the configuration of the PLL portion in FIG. 8. FIG. 10 is a diagram illustrating a configuration different from that of FIG. 9.

The internal oscillator of the PLL 140 is the VCO 147, whose output is subjected to a phase comparison with a signal from the timing extractor 141 to synchronize the VCO 147. By disconnecting the connection between the LPF 145 and the VCO 147 once the PLL 140 is locked, as shown in FIGS. 9 and 10, the voltage in the locked state can be maintained.

If the detection object 105 has a function for external communication, the switching timing can be directly determined by transmitting a communication signal with the switching signal superimposed thereon.

Third Embodiment

Next, a third embodiment of the present invention will be described with reference to FIGS. 11 and 12.

A position detection system of this embodiment has the same basic configuration as that of the second embodiment, but differs from that of the second embodiment in the method for distinguishing between calibration and position measurement. In this embodiment, therefore, only the method for distinguishing between calibration and position measurement will be described using FIGS. 11 and 12, and the other components etc. will not be described.

Figure 11:
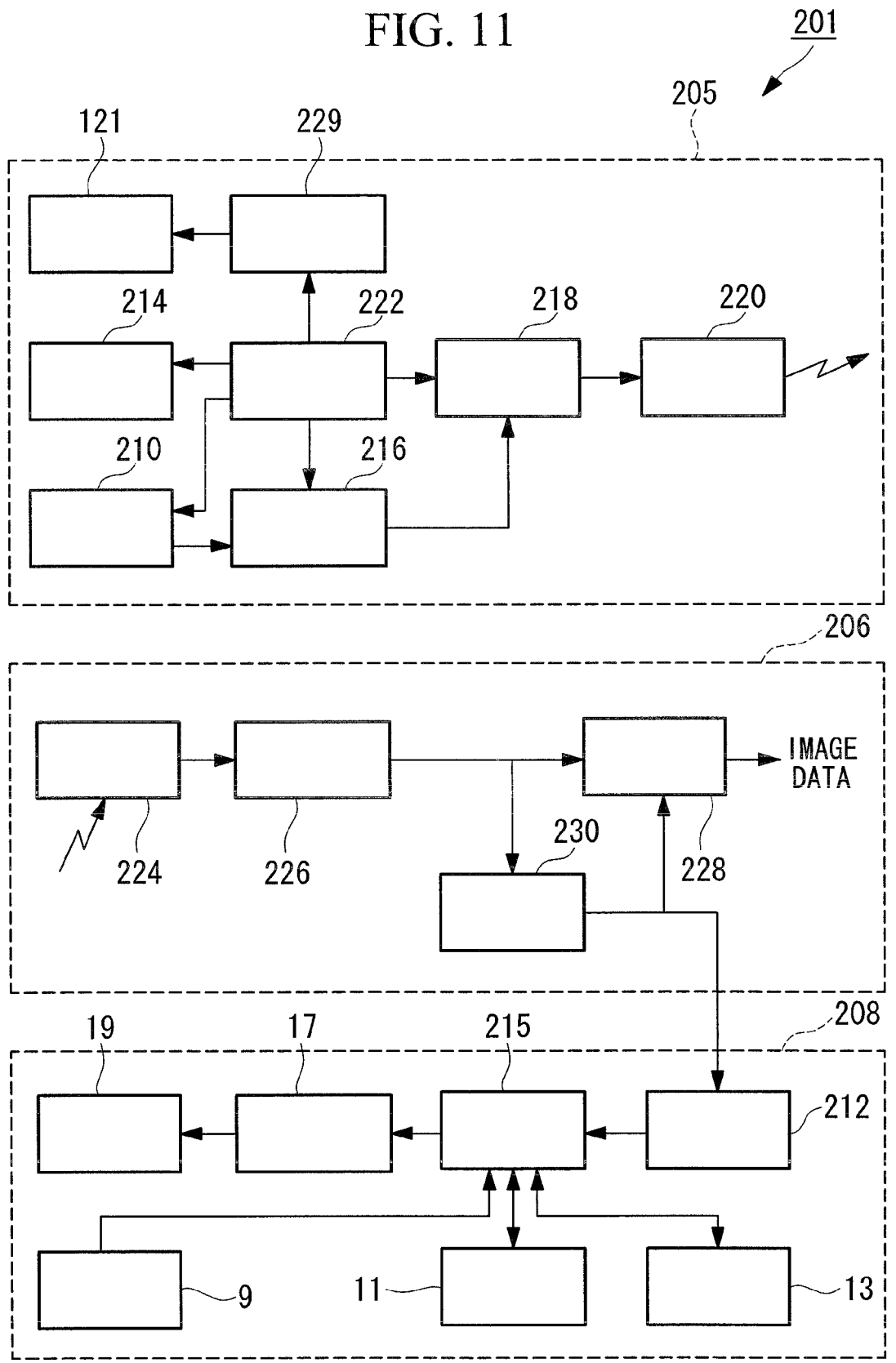
FIG. 11 is a block diagram outlining a position detection system according to a third embodiment of the present invention.

FIG. 11 is a block diagram outlining a position detection system according to this embodiment.

The same components as in the second embodiment are indicated by the same reference signs and will not be described.

As shown in FIG. 11, a position detection system (position detection system for a detection object) 201 includes a detection object 205 that is a capsule endoscope, an extracorporeal device 206 that processes an image captured by the detection object 205, and a position detection device 208 that calculates the position of the detection object 205.

The detection object 205 includes an image-capturing section 210 that captures a video image outside the detection object 205; an illuminating section 214 that illuminates a region to be imaged; a detection-object-side signal-processing section 216 that subjects the acquired image-capturing data to conversion processes; a transmitting section 218 and a detection-object-side antenna 220 that transmit the image-capturing data subjected to the conversion processes to the extracorporeal device 206 as a wireless signal; a switching-signal generating section (switch-controlling unit) 229 that generates a switching signal at a timing corresponding to a vertical synchronization signal with respect to the image-capturing data; a resonant circuit 121; and an image-capturing controlling section 222 that controls the image-capturing section 210, the illuminating section 214, the detection-object-side signal-processing section 216, the transmitting section 218, and the switching-signal generating section 229.

The extracorporeal device 206 includes an extracorporeal-device-side antenna 224 and a receiving section 226 that receive and demodulate the wireless signal transmitted from the detection object 205; an extracorporeal-device-side signal-processing section 228 that extracts the image-capturing data from the demodulated signal; and a synchronization-processing section 230 that extracts a synchronization signal from the decoded signal.

The position detection device 208 includes a switching-signal extracting section 212 to which the synchronization signal is input from the extracorporeal device 206; a position-detection-magnetic-field detecting section 9 that detects a position-detection magnetic field, or a position-detection magnetic field and a resonant magnetic field; a memory 13 that stores a detection signal; a position-calculating section 11 that calculates the position and orientation of the detection object 205; a position-detection controlling section 215 that controls, for example, a position-detection-signal generating section 17, the position-calculating section 11, and the memory 13; the position-detection-signal generating section 17, which generates an alternating signal; and a position-detection-magnetic-field generating section 19 that generates the position-detection magnetic field based on the alternating signal.

Next, a feature of the position detection system 201 according to this embodiment, namely, the method for calibration after the introduction of the detection object 205 into the operating region, will be described. The calibration method and the position detection method according to this embodiment will not be described because they are similar to those of the first embodiment.

If the detection object 205 is activated, as shown in FIG. 11, the illuminating section 214 illuminates the region to be imaged on a timing generated by the image-capturing controlling section 222, and the image-capturing section 210 captures a video image. The detection-object-side signal-processing section 216 then converts the acquired image-capturing data into a data format compatible with transmission from the transmitting section 218. For example, the data is subjected to conversion processes such as data compression, error correction code addition, and modulation.

The switching-signal generating section 229, on the other hand, generates a switching signal on the timing generated by the image-capturing controlling section 222 to switch the resonant circuit 121 ON or OFF.

The timing generated by the image-capturing controlling section can be exemplified by the timing of a vertical synchronization signal with respect to the video image.

The wireless signal transmitted from the transmitting section 218 is received by the extracorporeal-device-side antenna 224 and is demodulated by the receiving section 226. The demodulated signal is input to the synchronization-processing section 230 and the extracorporeal-device-side signal-processing section 228. The synchronization-processing section 230 extracts the synchronization signal (the vertical synchronization signal with respect to the video image in this embodiment) from the demodulated signal and inputs it to the extracorporeal-device-side signal-processing section 228 and the switching-signal extracting section 212. The extracorporeal-device-side signal-processing section 228 extracts the image-capturing data from the decoded signal based on the synchronization signal.

The switching-signal extracting section 212 extracts the switching signal from the input synchronization signal and inputs it to the position-detection controlling section 215. The position-detection controlling section 215 detects switching between calibration and position detection of the detection object 205 based on the input switching signal.

The position-detection controlling section 215 distinguishes between calibration and position detection of the detection object 205 based on the difference between detection signals from the position-detection-magnetic-field detecting section 9 before and after switching. Specifically, as shown in FIG. 4, if the amplitude of the detection signal from the position-detection-magnetic-field detecting section 9 during position detection of the detection object 205 is lower than that of the detection signal during calibration, the difference is a negative value for position detection of the detection object 205 and is a positive value for calibration. With this difference, calibration and position detection of the detection object 205 can be distinguished.

A time delay due to the modulation and demodulation of the image-capturing data results in a time difference from position detection of the detection object 205. It is therefore desirable to establish synchronization by factoring in the time difference as a specified value.

FIG. 12 is a block diagram outlining a modification of the position detection system in FIG. 11.

The switching between calibration and position detection of the detection object 205 may be detected either from a vertical synchronization signal with respect to image-capturing data, as in the above embodiment, or from a switching signal generated by the switching-signal generating section 229 of the detection object 205 and transmitted after being superimposed on the image-capturing data, as shown in FIG. 12; the detection method is not particularly limited.

A modification in which a switching signal is transmitted after being superimposed on image-capturing data will now be described with reference to FIG. 12.

The same components as in the third embodiment are indicated by the same reference signs and will not be described.

As shown in FIG. 12, a position detection system (position detection system for a detection object) 301 includes a detection object 305 that is a capsule endoscope, an extracorporeal device 306 that processes an image captured by the detection object 305, and a position detection device 308 that calculates the position of the detection object 305.

The detection object 305 includes an image-capturing section 210; an illuminating section 214; a detection-object-side signal-processing section 216; a data-synthesizing section 317 that superimposes a switching signal on image-capturing data subjected to conversion processes; a transmitting section 218 and a detection-object-side antenna 220 that transmit the superimposed signal to the extracorporeal device 306 as a wireless signal; a switching-signal generating section 229; a resonant circuit 121; and an image-capturing controlling section 222 that controls the image-capturing section 210, the illuminating section 214, the detection-object-side signal-processing section 216, the transmitting section 218, and the switching-signal generating section 229.

The extracorporeal device 306 includes an extracorporeal-device-side antenna 224 and a receiving section 226 that receive and demodulate the wireless signal transmitted from the detection object 305; an extracorporeal-device-side signal-processing section 228 that extracts the image-capturing data from the demodulated signal; and a synchronization-processing section 330 that extracts the switching signal from the decoded signal.

The position detection device 308 includes a position-detection-magnetic-field detecting section 9; a memory 13; a position-calculating section 11; a position-detection controlling section 315 that controls, for example, a position-detection-signal generating section 17, the position-calculating section 11, and the memory 13; the position-detection-signal generating section 17; and a position-detection-magnetic-field generating section 19.

Next, a feature of the position detection system 301 according to this embodiment, namely, the method for calibration after the introduction of the detection object 305 into the operating region, will be described. The calibration method and the position detection method according to this embodiment will not be described because they are similar to those of the first embodiment.

If the detection object 305 is activated, as in the third embodiment, the image-capturing section 210 captures an image, and the image-capturing data is converted into a data format compatible with transmission.

The switching-signal generating section 229, on the other hand, generates a switching signal on a timing generated by the image-capturing controlling section 222 to switch the resonant circuit 121 ON or OFF and also inputs it to the data-synthesizing section 317.

The data-synthesizing section 317 generates a signal by superimposing the switching signal on the converted image-capturing data, and the generated signal is transmitted from the transmitting section 218 as a wireless signal. The synthesis method involves specifying its arrangement as a data format.

The wireless signal transmitted from the transmitting section 218 is received by the extracorporeal-device-side antenna 224 and is demodulated by the receiving section 226. The demodulated signal is input to the synchronization-processing section 330 and the extracorporeal-device-side signal-processing section 228. The synchronization-processing section 330 extracts the switching signal from the demodulated signal and inputs it to the extracorporeal-device-side signal-processing section 228. The extracorporeal-device-side signal-processing section 228 extracts the image-capturing data from the decoded signal based on the switching signal. The extracorporeal-device-side signal-processing section 228 inputs the switching signal to the position-detection controlling section 315.

The position-detection controlling section 315 detects switching between calibration and position detection of the detection object 305 based on the input switching signal.

In this modification, unlike the third embodiment, calibration and position detection of the detection object 305 are distinguished based on the switching signal; they are not distinguished based on the difference between detection signals from the position-detection-magnetic-field detecting section 9 before and after switching.

In this modification, as in the third embodiment, a time delay due to the modulation and demodulation of the image-capturing data results in a time difference from position detection of the detection object 305. It is therefore desirable to establish synchronization by factoring in the time difference as a specified value.

The invention claimed is:

1. A position detection system for a detection object, comprising:
a magnetic-field generating unit including a position-detection-signal generating section that generates an alternating signal of predetermined frequency and a position-detection-magnetic-field generating section that generates a position-detection magnetic field based on the alternating signal;
a detection object including a coil and a capacitor constituting a resonant circuit and an external-signal switch that connects or disconnects the path of the resonant circuit based on an external signal, the detection object generating a resonant magnetic field by causing resonance when a current flows through the resonant circuit in response to the position-detection magnetic field;
a switch-controlling unit including a switching-signal generating section that generates a switching signal for controlling connecting or disconnecting of the external-signal switch and a switching-signal transmitting section that transmits the generated switching signal to the external-signal switch by converting the switching signal into physical energy;
a position-detection-magnetic-field detecting unit that detects the magnetic field strength of the position-detection magnetic field and the resonant magnetic field;
a position-calculating unit that calculates the position and orientation of the detection object based on a detection signal from the position-detection-magnetic-field detecting unit;
a memory that stores the detection signal from the position-detection-magnetic-field detecting unit; and
a position-detection controlling unit that stores the detection signal from the position-detection-magnetic-field detecting unit in the memory separately divided into a detection signal resulting from detection of the position-detection magnetic field alone and a detection signal resulting from detection of the position-detection magnetic field and the resonant magnetic field.

2. The position detection system for the detection object according to claim 1, wherein the external-signal switch connects or disconnects the path of the resonant circuit in response to a switching signal converted into a magnetic field.

3. A position detection system for a detection object, comprising:
a magnetic-field generating unit including a position-detection-signal generating section that generates an alternating signal of predetermined frequency and a position-detection-magnetic-field generating section that generates a position-detection magnetic field based on the alternating signal;
a detection object including a coil and a capacitor constituting a resonant circuit and an internal-signal switch that connects or disconnects the path of the resonant circuit based on an internal signal, the detection object generating a resonant magnetic field by causing resonance when a current flows through the resonant circuit in response to the position-detection magnetic field;
a switch-controlling unit disposed inside the detection object and including a switching-signal generating section that generates a switching signal for controlling connecting or disconnecting of the internal-signal switch;
a position-detection-magnetic-field detecting unit that detects the magnetic field strength of the position-detection magnetic field and the resonant magnetic field;
a position-calculating unit that calculates the position and orientation of the detection object based on a detection signal from the position-detection-magnetic-field detecting unit;
a switching-signal extracting unit that extracts the switching signal by detecting a level change of the detection signal;
a memory that stores the detection signal from the position-detection-magnetic-field detecting unit; and
a position-detection controlling unit that stores the detection signal from the position-detection-magnetic-field detecting unit in the memory separately divided into a detection signal resulting from detection of the position-detection magnetic field alone and a detection signal resulting from detection of the position-detection magnetic field and the resonant magnetic field.

4. The position detection system for the detection object according to claim 1, wherein the position-detection controlling unit controls the position-detection-signal generating section.

5. The position detection system for the detection object according to claim 1, wherein the detection signal acquired by the position-detection-magnetic-field detecting unit this time is written over a detection signal previously acquired by the position-detection-magnetic-field detecting unit and stored in the memory.

6. The position detection system for the detection object according to claim 1, wherein the detection object includes a permanent magnet to which an external magnetic field for posture control is applied to control the posture of the detection object.

7. The position detection system for the detection object according to claim 2, wherein the detection object includes a permanent magnet to which an external magnetic field for posture control is applied to control the posture of the detection object.

8. The position detection system for the detection object according to claim 3, wherein the detection object includes a permanent magnet to which an external magnetic field for posture control is applied to control the posture of the detection object.

9. The position detection system for the detection object according to claim 7, wherein the switching signal converted into a magnetic field has a higher frequency than the magnetic field for posture control.

10. The position detection system for the detection object according to claim 3, wherein the switching-signal generating section comprises a phase-locked loop.

11. The position detection system for the detection object according to claim 1, wherein
the detection object is a capsule endoscope that is introduced into a body; and
the capsule endoscope includes a transmitting section that wirelessly transmits an image captured inside the body by an image-capturing section to an extracorporeal device.

12. The position detection system for the detection object according to claim 3, wherein
the detection object is a capsule endoscope that is introduced into a body; and
the capsule endoscope includes a transmitting section that wirelessly transmits an image captured inside the body by an image-capturing section to an extracorporeal device.

13. The position detection system for the detection object according to claim 12, wherein
the switching signal is generated on a timing when the image is captured, and the image is transmitted to the extracorporeal device as a wireless signal; and
the switching-signal extracting unit extracts the switching signal from the wireless signal transmitted to the extracorporeal device.

14. The position detection system for the detection object according to claim 12, wherein
the capsule endoscope superimposes the switching signal on an image signal acquired by the image capturing and transmits the signal to the extracorporeal device as a wireless signal; and
the extracorporeal device extracts the switching signal from the wireless signal and outputs the switching signal to the position-detection controlling unit.

15. A position detection method for detecting the position of a detection object including a coil and a capacitor constituting a resonant circuit and an external-signal switch that connects or disconnects the path of the resonant circuit based on a switching signal, the detection object generating a resonant magnetic field by causing resonance when a current flows through the resonant circuit in response to a position-detection magnetic field, the method comprising:
generating the switching signal for controlling connecting or disconnecting of the external-signal switch from a switching-signal generating section of a switch-controlling unit disposed outside the detection object and transmitting the switching signal to the external-signal switch by converting the switching signal into physical energy in a switching-signal transmitting section;
generating an alternating signal of predetermined frequency from a position-detection-signal generating section of a magnetic-field generating unit and generating the position-detection magnetic field based on the alternating signal from a position-detection-magnetic-field generating section;
detecting the magnetic field strength of the position-detection magnetic field and the resonant magnetic field in a position-detection-magnetic-field detecting unit;
calculating the position and orientation of the detection object based on a detection signal detected by the position-detection-magnetic-field detecting unit in a position-calculating unit; and
storing the detection signal detected by the position-detection-magnetic-field detecting unit in a memory separately divided into a detection signal resulting from detection of the position-detection magnetic field alone and a detection signal resulting from detection of the position-detection magnetic field and the resonant magnetic field.

16. A position detection method for detecting the position of a detection object including a coil and a capacitor constituting a resonant circuit and an internal-signal switch that connects or disconnects the path of the resonant circuit based on a switching signal, the detection object generating a resonant magnetic field by causing resonance when a current flows through the resonant circuit in response to a position-detection magnetic field, the method comprising:
generating the switching signal for controlling connecting or disconnecting of the internal-signal switch from a switching-signal generating section of a switch-controlling unit disposed inside the detection object;
generating an alternating signal of predetermined frequency from a position-detection-signal generating section of a magnetic-field generating unit and generating the position-detection magnetic field based on the alternating signal from a position-detection-magnetic-field generating section;
detecting the magnetic field strength of the position-detection magnetic field and the resonant magnetic field in a position-detection-magnetic-field detecting unit;
calculating the position and orientation of the detection object based on a detection signal detected by the position-detection-magnetic-field detecting unit in a position-calculating unit;
extracting the switching signal by detecting a level change of the detection signal in a switching-signal extracting unit; and storing the detection signal detected by the position-detection-magnetic-field detecting unit in a memory separately divided into a detection signal resulting from detection of the position-detection magnetic field alone and a detection signal resulting from detection of the position-detection magnetic field and the resonant magnetic field.

17. The position detection method for the detection object according to claim 16, wherein the switching signal is superimposed on an image signal acquired by an image-capturing section disposed in the detection object and is transmitted to an extracorporeal device as a wireless signal; and the switching signal is extracted from the wireless signal in the extracorporeal device and is output to a position-detection controlling unit.

* * * * *